United States Patent
Hennies et al.

(10) Patent No.: US 7,342,025 B2
(45) Date of Patent: *Mar. 11, 2008

(54) SUBSTITUTED C-IMIDAZO[1,2-A]PYRIDIN-3-YL-METHYLAMINES

(75) Inventors: Hagen-Heinrich Hennies, Simmerath (DE); Corinna Sundermann, Aachen (DE); Bernd Sundermann, Aachen (DE); Stefan Oberboersch, Aachen (DE)

(73) Assignee: Gruenenthal GmbH, Aachen (DE)

( * ) Notice: Subject to any disclaimer, the term of this patent is extended or adjusted under 35 U.S.C. 154(b) by 124 days.

This patent is subject to a terminal disclaimer.

(21) Appl. No.: 11/100,535

(22) Filed: Apr. 7, 2005

(65) Prior Publication Data

US 2005/0239822 A1    Oct. 27, 2005

Related U.S. Application Data

(63) Continuation of application No. PCT/EP03/011011, filed on Oct. 6, 2003.

(30) Foreign Application Priority Data

Oct. 8, 2002    (DE)    ................ 102 46 890

(51) Int. Cl.
*A01N 43/42* (2006.01)
*A61K 31/44* (2006.01)
*C07D 471/02* (2006.01)
*C07D 491/02* (2006.01)
*C07D 498/02* (2006.01)

(52) U.S. Cl. ...................... 514/300; 546/121
(58) Field of Classification Search ................ 546/118, 546/121; 514/300
See application file for complete search history.

(56) References Cited

U.S. PATENT DOCUMENTS

2002/0042420 A1    4/2002    Briem et al.
2005/0239823 A1*  10/2005    Oberboersch et al. ...... 514/303

FOREIGN PATENT DOCUMENTS

| DE | 197 34 184 A1 | 2/1999 |
| FR | 1 536 351 | 7/1968 |
| WO | WO 96/34866 A1 | 11/1996 |
| WO | WO 01/27109 A2 | 4/2001 |
| WO | WO 02/14313 A2 | 2/2002 |
| WO | WO 02/066477 A2 | 8/2002 |
| WO | WO 02/066478 A1 | 8/2002 |

OTHER PUBLICATIONS

CASREACT 65:3958, abstract only of Almirante et al,. bollettino Chimico Farmaceutico, 1966, vol. 105, pp. 32-44.*
Freshney, Culture of animal cells, a manual of basic technique, 1983, pp. 1-6.□□.*
Dermer et al, Bio/Technology, vol. 12, pp. 320, 1994.*
International Search Report dated Feb. 10, 2004 (Two (2) pages).
German Search Report dated Jun. 3, 2003 with English translation of relevant portion (Eight (8) pages).
Kamisnki, et al., "Antiulcer Agents. 2. Gastric Antisecretory, Cytoprotective, and Metabolic Properties of Substituted Imidazo[1,2-a]pyridines and Analogues", *J. Med. Chem*, vol. 30, 1987, pp. 2031-2046.
Almirante, et al., "Syntheses and Reactions of Imidazoles", *Bollettino Chimico Farmaceutico*, vol. 105, No. 1, 1966.
L. H. Lassen, et al., "Nitric oxide synthase inhibition in migraine" The Lancet, vol. 349, Feb. 8, 1997, pp. 401-402.
Lars Lykke Thomsen, et al., "Nitric Oxide Theory of Migraine" Clinical Neuroscience, vol. 5, 1998, pp. 28-33.
P. E. Chabrier, et al., "Nitric oxide synthases: targets for therapeutic strategies in neurological diseases" CMLS, Cell. Mol. Life Science, vol. 55, 1999, pp. 1029-1035.
I. C. Green, et al., "Nitric oxide: from basic research to clinical applications" DDT, vol. 4, No. 2, Feb. 1999, pp. 47-49.
Adrian J. Hobbs, et al., "Inhibition of Nitric Oxide Synthase as a Potential Therapeutic Target" Annu. Rev. Pharmacol. Toxicol, vol. 39, 1999, pp. 191-220.
Houben-Weyl, "1.4.3.5 Addition of Enamines to Iminium Ions", vol. E 21, pp. 1925-1929.
Merla et al., "Efficient Synthesis of γ-Oxo- and γ-Hydroxy-α-amino Acids", *Synthesis*, Nov. 1998, pp. 1609-1614.
Ferid Murad, "Discovery of Some of the Biological Effects of Nitric Oxide and Its Role in Cell Signaling (Nobel Lecture)" Angew. Chem. Int. Ed., vol. 38, 1999, pp. 1857-1868.
Louis J. Ignarro, "Stickstoffmonoxid: ein einzigartiges endogenes Signalmolekuel in der Gefaessbiologie (Nobel-Vortrag)" Angew. Chem. vol. 111, 1999, pp. 2002-2013.

* cited by examiner

*Primary Examiner*—Margaret D. Seaman
*Assistant Examiner*—Niloofar Rahmani
(74) *Attorney, Agent, or Firm*—Crowell & Moring LLP

(57) ABSTRACT

Substituted C-imidazo [1,2-a]pyridine-3-yl methylamines and physiologically acceptable salts thereof, a method for the production thereof, pharmaceutical compositions containing these compounds, and pharmaceutical uses thereof, e.g., as NO synthase inhibitors.

14 Claims, No Drawings

SUBSTITUTED C-IMIDAZO[1,2-A]PYRIDIN-3-YL-METHYLAMINES

CROSS REFERENCE TO RELATED APPLICATIONS

This application is a continuation of international patent application no. PCT/EP2003/011011, filed Oct. 6, 2003, designating the United States of America, and published in German on Apr. 22, 2004 as WO 2004/033453, the entire disclosure of which is incorporated herein by reference. Priority is claimed based on Federal Republic of Germany patent application no. DE 102 46 890.7, filed Oct. 8, 2002.

BACKGROUND OF THE INVENTION

The present invention relates to substituted C-imidazo[1,2-a]pyridin-3-yl-methylamines and their physiologically acceptable salts, processes for their preparation, medicaments comprising these compounds and the use of substituted C-imidazo[1,2-a]pyridin-3-yl-methylamines for the preparation of medicaments.

Nitrogen monoxide (NO) regulates numerous physiological processes, inter alia neurotransmission, relaxation and proliferation of the smooth musculature, adhesion and aggregation of thrombocytes as well as tissue injury and inflammation. On the basis of the large number of signal functions, nitrogen monoxide is associated with a number of diseases, for example in L. J. Ignarro, Angew. Chem. (1999), 111, pages 2002-2013 and in F. Murad, Angew. Chem. Int. Ed. (1999), 111, pages 1976-1989. The enzyme which is responsible for the physiological formation of nitrogen monoxide, nitrogen monoxide synthase (NO synthase), plays an important role in this context in the therapeutic influencing of these diseases. Three different iso forms of NO synthase have so far been identified, namely the two constitutive forms nNO synthase and eNO synthase and the inducible form iNO synthase (A. J. Hobbs, A. Higgs, S. Moncada, Annu. Rev. Pharmacol. Toxicol. (1999), 39, pages 191-220; I. C. Green, P.-E. Chabrier, DDT (1999), 4, pages 47-49; P.-E. Chabrier et al., Cell. Mol. Life Sci. (1999), 55, pages 1029-1035).

The inhibition of NO synthase opens up new therapy schemes for various diseases associated with nitrogen monoxide (A. J. Hobbs et al., Annu. Rev. Pharmacol. Toxicol. (1999), 39, pages 191-220; I. C. Green, P.-E. Chabrier, DDT (1999), 4, pages 47-49; P.-E. Chabrier et al., Cell. Mol. Life Sci. (1999), 55, pages 1029-1035), such as, for example, migraine (L. L. Thomsen, J. Olesen, Clinical Neuroscience (1998), 5, pages 28-33; L. H. Lassen et al., The Lancet (1997), 349, 401-402), septic shock, neurodegenerative diseases, such as multiple sclerosis, Parkinson's disease, Alzheimer's disease or Huntington's disease, inflammations, inflammatory pain, cerebral ischaemia, diabetes, meningitis and arteriosclerosis. Furthermore, inhibition of NO synthase can have an effect on wound healing, on tumours and on angiogenesis, and can cause a non-specific immunity to microorganisms (A. J. Hobbs et al., Annu. Rev. Pharmacol. Toxicol. (1999), 39, pages 191-220).

Active compounds known to date which inhibit NO synthase include, in addition to L-NMMA and L-NAME—i.e. analogues of L-arginine from which nitrogen monoxide and citrulline are formed in vivo with the involvement of NO synthase—inter alia S-methyl-L-citrulline, aminoguanidine, S-methylisourea, 7-nitroindazole and 2-mercaptoethylguanidine (A. J. Hobbs et al., Annu. Rev. Pharmacol. Toxicol. (1999), 39, pages 191-220).

SUMMARY OF THE INVENTION

An object of the present invention was therefore to provide new substances which act as an inhibitor on nitrogen monoxide synthase.

A further object of the invention is to provide pharmaceutical compositions which are suitable for the treatment of migraine, septic shock, neurodegenerative diseases, such as multiple sclerosis, Parkinson's disease, Alzheimer's disease or Huntington's disease, inflammations, inflammatory pain, cerebral ischaemia, diabetes, meningitis, arteriosclerosis, cancer diseases or fungal diseases or for wound healing.

In accordance with the present invention it has now been found that substituted C-imidazo[1,2-a] pyridin-3-yl-methylamines corresponding to the following formula I act as inhibitors of nitrogen monoxide synthase and are suitable in particular for the treatment of migraine, septic shock, neurodegenerative diseases, such as multiple sclerosis, Parkinson's disease, Alzheimer's disease or Huntington's disease, inflammations, inflammatory pain, cerebral ischaemia, diabetes, meningitis, arteriosclerosis, cancer diseases or fungal diseases or for wound healing.

The present invention therefore provides substituted C-imidazo[1,2-a]pyridin-3-yl-methylamines corresponding to formula I

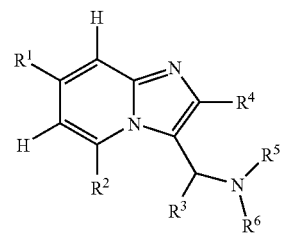

wherein in each case $R^1$ represents OH, SH, $NH_2$, $NHCH_3$, $N(CH_3)_2$, $CH_3$, $CH_2Cl$, $CH_2F$, $CHF_2$, $CF_3$, $OCH_3$, $OCH_2Cl$, $OCH_2F$, $OCHF_2$, $OCF_3$, $C_2H_5$, $CHClCH_3$, $CH_2CH_2Cl$, $CHFCH_3$, $CH_2CH_2F$, $CH_2CHF_2$, $CH_2CF_3$, $OC_2H_5$, COOH, $CH_2OH$, $CHOHCH_3$, $CH_2CH_2OH$, F, Br, I or Cl, $R^2$ represents H or $CH_3$, $R^3$ represents H; $C_{1-6}$-alkyl, mono- or polysubstituted or unsubstituted, saturated or unsaturated, branched or unbranched; methyl, ethyl, methylethyl, 1,1-dimethylethyl, propyl, 2-methylpropyl, 1-methylpropyl, 1-ethylpropyl, butyl, i-butyl, n-butyl, tert-butyl, 1-methylbutyl, 2-methylbutyl, 3-methylbutyl, 2,2-dimethylbutyl, pentyl, 2-methylpentyl, 3-methylpentyl, 1,1-dimethylpropyl, 1,2-dimethylpropyl, 2,2-dimethylpropyl, 1-ethylpropyl or hexyl, in each case mono- or polysubstituted or unsubstituted, branched or unbranched, or in each case optionally mono- or polysubstituted or unsubstituted, branched or unbranched; $C_{3-8}$-cycloalkyl, in each case mono- or polysubstituted or unsubstituted, monounsaturated or saturated; cyclopropyl, cyclobutyl, cyclopentyl, cyclohexyl, cycloheptyl, cyclooctyl, 2-methylcyclopropyl, cyclopropylmethyl, 2-methylcyclobutyl, 3-methylcyclobutyl, cyclobutylmethyl, in each case substituted or unsubstituted; or aryl or heteroaryl, in each case substituted or unsubstituted; or COOR$^{10}$, R$^4$ represents H; C$_{1-12}$-alkyl, mono- or polysubstituted or unsubstituted, saturated or unsaturated, branched or unbranched; methyl, ethyl, methylethyl, 1,1-dimethylethyl, propyl, 2-methylpropyl, 1-methylpropyl, 1-ethylpropyl, butyl, i-butyl, n-butyl, tert-butyl, 1-methylbutyl, 2-methylbutyl, 3-methylbutyl, 2,2-dimethylbutyl, pentyl, 2-methylpentyl, 3-methylpentyl, 1,1-dimethylpropyl, 1,2-dimethylpropyl, 2,2-dimethylpropyl, 1-ethylpropyl or hexyl, heptyl, octyl, nonyl, decyl, undecyl, dodecyl, in each case mono- or polysubstituted or unsubstituted, branched or unbranched, or in each case optionally mono- or polysubstituted or unsubstituted, branched or unbranched; C$_{3-8}$-cycloalkyl, in each case mono- or polysubstituted or unsubstituted, monounsaturated or saturated; cyclopropyl, cyclobutyl, cyclopentyl, cyclohexyl, cycloheptyl, cyclooctyl, 2-methylcyclopropyl, cyclopropylmethyl, 2-methylcyclobutyl, 3-methylcyclobutyl, cyclobutylmethyl, in each case substituted or unsubstituted; or a radical corresponding to formula II

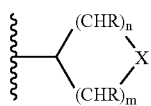

wherein in each case
n represents a number from 0 to 6,
m represents a number from 0 to 6,
$1 \leq m+n \leq 6$,
X represents O, S, SO, SO$_2$ or NR$^7$, and
each R independently represents H, F, Br, I, Cl, OH, SH, NH$_2$, NO$_2$, CH$_3$, C$_2$H$_5$, OCH$_3$, OC$_2$H$_5$, or OCF$_3$;

R$^5$ represents H; C$_{1-6}$-alkyl, mono- or polysubstituted or unsubstituted, saturated or unsaturated, branched or unbranched; methyl, ethyl, methylethyl, 1,1-dimethylethyl, propyl, 2-methylpropyl, 1-methylpropyl, 1-ethylpropyl, butyl, i-butyl, n-butyl, tert-butyl, 1-methylbutyl, 2-methylbutyl, 3-methylbutyl, 2,2-dimethylbutyl, pentyl, 2-methylpentyl, 3-methylpentyl, 1,1-dimethylpropyl, 1,2-dimethylpropyl, 2,2-dimethylpropyl, 1-ethylpropyl or hexyl, in each case mono- or polysubstituted or unsubstituted, branched or unbranched, or in each case optionally mono- or polysubstituted or unsubstituted, branched or unbranched; or C$_{3-8}$-cycloalkyl, in each case mono- or polysubstituted or unsubstituted, monounsaturated or saturated; cyclopropyl, cyclobutyl, cyclopentyl, cyclohexyl, cycloheptyl, cyclooctyl, 2-methylcyclopropyl, cyclopropylmethyl, 2-methylcyclobutyl, 3-methylcyclobutyl, cyclobutylmethyl in each case substituted or unsubstituted;

R$^6$ represents H; H; C$_{1-6}$-alkyl, mono- or polysubstituted or unsubstituted, saturated or unsaturated, branched or unbranched; methyl, ethyl, methylethyl, 1,1-dimethylethyl, propyl, 2-methylpropyl, 1-methylpropyl, 1-ethylpropyl, butyl, i-butyl, n-butyl, tert-butyl, 1-methylbutyl, 2-methylbutyl, 3-methylbutyl, 2,2-dimethylbutyl, pentyl, 2-methylpentyl, 3-methylpentyl, 1,1-dimethylpropyl, 1,2-dimethylpropyl, 2,2-dimethylpropyl, 1-ethylpropyl or hexyl, in each case mono- or polysubstituted or unsubstituted, branched or unbranched, or in each case optionally mono- or polysubstituted or unsubstituted, branched or unbranched; or C$_{3-8}$-cycloalkyl, in each case mono- or polysubstituted or unsubstituted, monounsaturated or saturated; cyclopropyl, cyclobutyl, cyclopentyl, cyclohexyl, cycloheptyl, cyclooctyl, 2-methylcyclopropyl, cyclopropylmethyl, 2-methylcyclobutyl, 3-methylcyclobutyl, cyclobutyl, cyclobutylmethyl, in each case substituted or unsubstituted; or a radical according to formula IIa

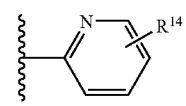

or the radicals R$^5$ and R$^6$ together form a ring and denote CH$_2$CH$_2$OCH$_2$CH$_2$, CH$_2$CH$_2$NR$^{11}$CH$_2$CH$_2$ or (CH$_2$)$_{3-6}$, R$^7$ represents H, a C$_{1-6}$-alkyl radical, preferably methyl, ethyl, propyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, 1-ethylpropyl or hexyl, a C$_{3-8}$-cycloalkyl radical, preferably cyclopropyl, 2-methylcyclopropyl, cyclopropylmethyl, cyclobutyl, 2-methylcyclobutyl, 3-methylcyclobutyl, cyclobutylmethyl, cyclopentyl, cyclohexyl or cyclooctyl, an acyl radical C(O)R$^8$ or a sulfonyl radical S(O$_2$)R$^9$, R$^8$ represents H, a C$_{1-6}$-alkyl radical or an aryl radical,
R$^9$ represents H, a C$_{1-6}$-alkyl radical or an aryl radical,
R$^{10}$ represents H, a C$_{1-6}$-alkyl radical or an aryl radical,
R$^{11}$ represents H, C$_{1-6}$-alkyl or C$_{3-8}$-cycloalkyl, aryl or heteroaryl, aryl or heteroaryl bonded via C$_{1-3}$-alkylene, acyl C(O)R$^{12}$ or sulfonyl S(O$_2$)R$^{13}$,
R$^{12}$ represents H, a C$_{1-6}$-alkyl radical or an aryl radical, and
R$^{14}$ represents H, F, Br, I, Cl, OH, SH, NH$_2$, NO$_2$, CH$_3$, C$_2$H$_5$, OCH$_3$, OC$_2$H$_5$, OCF$_3$;

optionally in the form of their racemates, their pure stereoisomers, in particular enantiomers or diastereomers, or in the form of mixtures of the stereoisomers, in particular the enantiomers or diastereomers, in any desired mixture ratio;

in the form shown or in the form of their acids or their bases or in the form of their salts, in particular the physiologically acceptable salts, or in the form of their solvates, in particular the hydrates;

with the proviso that the following compounds:

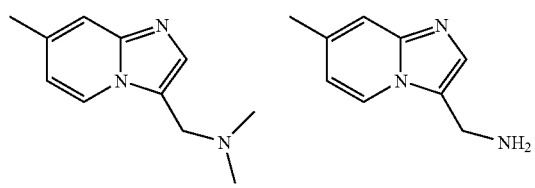

are excluded from the invention.

In the context of the present invention, the expression "C$_{1-12}$-alkyl radical" includes acyclic saturated or unsaturated hydrocarbon radicals, which can be branched- or straight-chain and unsubstituted or at least monosubstituted, having 1 to 6 carbon atoms. That is to say, in addition to C$_{1-12}$-alkanyls, C$_{2-12}$-alkenyls and C$_{2-12}$-alkynyls are also included, wherein the alkenyls have at least one carbon-carbon double bond and the alkynyls have at least one carbon-carbon triple bond. Preferably, the C$_{1-12}$-alkyl radical is selected from the group consisting of methyl, ethyl, n-propyl, 2-propyl, n-butyl, iso-butyl, sec-butyl, tert-butyl, n-pentyl, iso-pentyl, neo-pentyl, n-hexyl, 2-hexyl, n-octyl, ethenyl (vinyl), ethynyl, propenyl (—CH$_2$CH═CH$_2$, —CH═CH—CH$_3$, —C(═CH$_2$)—CH$_3$), propynyl (—CH—C≡CH, —C≡C—CH$_3$), butenyl, butynyl, pentenyl, pentynyl, hexenyl, hexynyl, octenyl and octynyl.

If the $C_{1-12}$-alkyl radical is mono- or polysubstituted, one or more hydrogen radical(s) is (are) preferably replaced by a substituent selected from the group consisting of F, Cl, Br, I, CN, NH$_2$, NH-alkyl, NH-aryl, NH-heteroaryl, NH-alkyl-aryl, NH-alkyl-heteroaryl, NH-heterocyclyl, NH-alkyl-OH, N(alkyl)$_2$, N(alkyl-aryl)$_2$, N(alkyl-heteroaryl)$_2$, N(heterocyclyl)$_2$, N(alkyl-OH)$_2$, NO, NO$_2$, SH, S-alkyl, S-aryl, S-heteroaryl, S-alkyl-aryl, S-alkyl-heteroaryl, S-heterocyclyl, S-alkyl-OH, S-alkyl-SH, OH, O-alkyl, O-aryl, O-heteroaryl, O-alkyl-aryl, O-alkyl-heteroaryl, O-heterocyclyl, O-alkyl-OH, CHO, C(═O)C$_{1-6}$-alkyl, C(═S)C$_{1-6}$-alkyl, C(═O)aryl, C(═S)aryl, C(═O)C$_{1-6}$-alkyl-aryl,

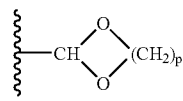

where p=1, 2 or 3, C(═S)C$_{1-6}$-alkyl-aryl, C(═O)-heteroaryl, C(═S)-heteroaryl, C(═O)-heterocyclyl, C(═S)-heterocyclyl, CO$_2$H, CO$_2$-alkyl, CO$_2$-alkyl-aryl, C(═O)NH$_2$, C(═O)NH-alkyl, C(═O)NHaryl, C(═O)NH-heterocyclyl, C(═O)N(alkyl)$_2$, C(═O)N(alkyl-aryl)$_2$, C(═O)N(alkyl-heteroaryl)$_2$, C(═O)N(heterocyclyl)$_2$, SO-alkyl, SO$_2$-alkyl, SO$_2$NH$_2$, SO$_3$H, cycloalkyl, aryl, heteroaryl and heterocyclyl, wherein polysubstituted C$_{1-6}$-alkyl radicals are to be understood as meaning those radicals which are poly- e.g. di- or trisubstituted either on different atoms or on the same atom of the C$_{1-6}$-alkyl radical, for example trisubstituted on the same carbon atom as in the case of CF$_3$ or —CH$_2$CF$_3$, or on different atoms as in the case of —CH(OH)—CH═CH—CHCl$_2$. The polysubstitution can be by the same or by different substituents. If the substituent itself contains an alkyl group, this is preferably selected from the group consisting of methyl, ethyl, CH$_2$OH and CF$_3$.

For the purposes of the present invention, the expression "C$_{3-8}$-cycloalkyl radical" includes cyclic hydrocarbons having 3 to 8 carbon atoms, which can be saturated or unsaturated, unsubstituted or at least monosubstituted, wherein bonding of the cycloalkyl radical to the basic skeleton of the general formula I can take place via any desired ring member of the cycloalkyl radical. The C$_{3-8}$-cycloalkyl radical is preferably selected from the group consisting of cyclopropyl, cyclobutyl, cyclopentyl, cyclohexyl, cycloheptyl, cyclooctyl, cyclopentenyl, cyclohexenyl, cycloheptenyl and cyclooctenyl. The C$_{3-8}$-cycloalkyl radical is particularly preferably a cyclohexyl radical.

In the context of the present invention, the expression "aryl radical" denotes aromatic hydrocarbons, which can also be fused with further saturated, at least partly unsaturated or aromatic ring systems, wherein bonding of the aryl radical to the basic skeleton of the general formula I can take place via any desired ring member of the aryl radical. If the aryl radical contains more than one substituent, these can be identical or different and can be in any desired and possible position of the aryl radical. The aryl radical is preferably selected from the group consisting of unsubstituted or at least monosubstituted phenyl, anthracenyl, 1-naphthyl and 2-naphthyl. The aryl radical is particularly preferably selected from the group consisting of phenyl, 3-hydroxyphenyl, 3-methoxyphenyl, 2,3-dihydroxyphenyl, 2,3-dimethoxyphenyl and 1-naphthyl.

If the C$_{3-8}$-cycloalkyl or the aryl radical is mono- or polysubstituted, this is preferably understood as meaning mono- or poly-, e.g. di-, tri- or tetrasubstitution of one or more hydrogen atoms of the ring system by a substituent selected from the group consisting of F, Cl, Br, I, CN, NH$_2$, NH-alkyl, NH-aryl, NH-heteroaryl, NH-alkyl-aryl, NH-alkyl-heteroaryl, NH-heterocyclyl, NH-alkyl-OH, N(alkyl)$_2$, N(alkyl-aryl)$_2$, N(alkyl-heteroaryl)$_2$, N(heterocyclyl)$_2$, N(alkyl-OH)$_2$, NO, NO$_2$, SH, S-alkyl, S-cycloalkyl, S-aryl, S-heteroaryl, S-alkyl-aryl, S-alkyl-heteroaryl, S-heterocyclyl, S-alkyl-OH, S-alkyl-SH, OH, O-alkyl, O-cycloalkyl, O-aryl, O-heteroaryl, O-alkyl-aryl, O-alkyl-heteroaryl, O-heterocyclyl, O-alkyl-OH, CHO, C(═O)C$_{1-6}$-alkyl, C(═S)C$_{1-6}$-alkyl, C(═O)aryl, C(═S)aryl, C(═O)-C$_{1-6}$-alkyl-aryl,

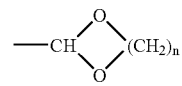

where n=1, 2 or 3, C(═S)C$_{1-6}$-alkyl-aryl, C(═O)-heteroaryl, C(═S)-heteroaryl, C(═O)-heterocyclyl, C(═S)-heterocyclyl, CO$_2$H, CO$_2$-alkyl, CO$_2$-alkyl-aryl, C(═O)NH$_2$, C(═O)NH-alkyl, C(═O)NHaryl, C(═O)NH-heterocyclyl, C(═O)N(alkyl)$_2$, C(═O)N(alkyl-aryl)$_2$, C(═O)N(alkyl-heteroaryl)$_2$, C(═O)N(heterocyclyl)$_2$, S(O)-alkyl, S(O)-aryl, SO$_2$-alkyl, SO$_2$-aryl, SO$_2$NH$_2$, SO$_3$H, CF$_3$, ═O, ═S; alkyl, cycloalkyl, aryl, heteroaryl and heterocyclyl, wherein a substituent can optionally in its turn be substituted. The polysubstitution in this context is by identical or different substituents. For "aryl radicals", particularly preferred substituents are selected from the group consisting of F, CF$_3$, OH und O—CH$_3$. For "cycloalkyl radicals", particularly preferred substituents are CO$_2$H or CO$_2$ethyl.

In the context of the present invention, the expression "heteroaryl" represents a 5-, 6- or 7-membered cyclic aromatic radical which contains at least 1, optionally also 2, 3, 4 or 5 heteroatoms, wherein the heteroatoms can be identical or different and wherein bonding to the basic skeleton of the general formula I can take place via any desired and possible ring member of the heteroaryl radical. If the heteroaryl radical contains more than one substituent, these substituents on the heteroaryl can be identical or different and can be present in any desired and possible position of the heteroaryl. The heterocyclic radical can also be fused with further saturated, at least partly unsaturated or aromatic ring systems. Preferred heteroatoms are selected from the group consisting of nitrogen, oxygen and sulfur. The heteroaryl radical is preferably selected from the group consisting of unsubstituted or at least monosubstituted pyrrolyl, furyl, thienyl, pyrazolyl, imidazolyl, pyridinyl, pyridazinyl, pyrimidinyl, pyrazinyl, pyranyl, indolyl, indazolyl, purinyl, pyrimidinyl, indolizinyl, quinolinyl, isoquinolinyl, quinazolinyl, carbazolyl, phenazinyl and phenothiazinyl. Particularly preferred heteroaryl radicals are selected from the group consisting of pyridin-2-yl, pyridin-3-yl, furan-2-yl, furan-3-yl, 5-hydroxymethylene-furan-2-yl, 5-nitro-furan-2-yl, 5-[1,3]-dioxolane-furan-2-yl, 5-carboxy-furan-2-yl, thien-2-yl (2-thiophene), thien-3-yl (3-thiophene) and 5-carboxy-2-thiophene (5-carboxy-thien-2-yl).

In the context of the present invention, the expression "heterocyclyl" includes a 3-, 4-, 5-, 6- or 7-membered cyclic organic radical which contains at least 1, optionally also 2, 3, 4 or 5 heteroatoms in the ring system, wherein the heteroatoms can be identical or different and the cyclic radical is saturated or unsaturated, but not aromatic, and can be unsubstituted or at least monosubstituted. Bonding of the heterocyclyl radical to the basic skeleton of the general formula I can take place via any desired ring member of the heterocyclyl radical. The heterocyclyl radical can also be part of a bi- or polycyclic system. Preferred heteroatoms are selected from the group consisting of nitrogen, oxygen and sulfur. The $C_{3-7}$-heterocyclyl radical is preferably selected from the group consisting of tetrahydrofuryl, tetrahydropyranyl, pyrrolidinyl, piperidinyl, piperazinyl and morpholinyl.

If the compounds of formula I according to the invention or physiologically acceptable salts thereof have at least one asymmetric center, they can be in the form of their racemates, their pure enantiomers, their pure diastereomers or in the form of a mixture of at least two of the abovementioned stereoisomers. The substituted C-imidazo[1,2-a]pyridin-3-yl-methylamines of formula I can also be in the form of mixtures of their enantiomers or diastereomers. These mixtures can contain the particular stereoisomers in any desired mixture ratio. Preferably, chiral substituted C-imidazo[1,2-a]pyridin-3-yl-methylamines of formula I are used in the enantiomerically pure form.

In the context of this invention, alkyl and cycloalkyl radicals are also to be understood as meaning saturated and unsaturated (but not aromatic), branched, unbranched and cyclic hydrocarbons, which can be unsubstituted or mono- or polysubstituted. In this context, $C_{1-2}$-alkyl represents C1- or C2-alkyl, $C_{1-3}$-alkyl represents C1-, C2- or C3-alkyl, $C_{1-4}$-alkyl represents C1-, C2-, C3- or C4-alkyl, $C_{1-5}$-alkyl represents C1-, C2-, C3-, C4- or C5-alkyl, $C_{1-6}$-alkyl represents C1-, C2-, C3-, C4-, C5- or C6-alkyl, $C_{1-7}$-alkyl represents C1-, C2-, C3-, C4-, C5-, C6- or C7-alkyl, $C_{1-8}$-alkyl represents C1-, C2-, C3-, C4-, C5-, C6-, C7- or C8-alkyl, $C_{1-10}$-alkyl represents C1-, C2-, C3-, C4-, C5-, C6-, C7-, C8,- C9- or C10-alkyl and $C_{1-18}$-alkyl represents C1-, C2-, C3-, C4-, C5-, C6-, C7-, C8,- C9-, C10-, C11-, C12-, C13-, C14-, C15-, C16-, C17- or C18-alkyl. Furthermore, $C_{3-4}$-cycloalkyl represents C3- or C4-cycloalkyl, $C_{3-5}$-cycloalkyl represents C3-, C4- or C5-cycloalkyl, $C_{3-6}$-cycloalkyl represents C3-, C4-, C5- or C6-cycloalkyl, $C_{3-7}$-cycloalkyl represents C3-, C4-, C5- C6- or C7-cycloalkyl, $C_{3-8}$-cycloalkyl represents C3-, C4-, C5-, C6-, C7- or C8-cycloalkyl, $C_{4-5}$-cycloalkyl represents C4- or C5-cycloalkyl, $C_{4-6}$-cycloalkyl represents C4-, C5- or C6-cycloalkyl, $C_{4-7}$-cycloalkyl represents C4-, C5-, C6- or C7-cycloalkyl, $C_{5-6}$-cycloalkyl represents C5- or C6-cycloalkyl and $C_{5-7}$-cycloalkyl represents C5-, C6- or C7-cycloalkyl. With reference to cycloalkyl, the term also includes saturated cycloalkyls in which one or 2 carbon atoms are replaced by a heteroatom S, N or O. The term cycloalkyl also includes in particular, however, mono- or poly-, preferably monounsaturated cycloalkyls without a heteroatom in the ring, as long as the cycloalkyl is not an aromatic system. The alkyl and cycloalkyl radicals are preferably methyl, ethyl, vinyl (ethenyl), propyl, allyl (2-propenyl), 1-propynyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, cyclopropyl, 2-methylcyclopropyl, cyclopropylmethyl, cyclobutyl, cyclopentyl, cyclopentylmethyl, cyclohexyl, cycloheptyl, cyclooctyl, and also adamantyl, $CHF_2$, $CF_3$ or $CH_2OH$ as well as pyrazolinone, oxopyrazolinone, [1,4]dioxane or dioxolane.

In connection with alkyl and cycloalkyl here—unless expressly defined otherwise—in the context of this invention the term substituted is also understood as meaning substitution of at least one (optionally also more) hydrogen radical(s) by F, Cl, Br, I, $NH_2$, SH or OH, wherein "polysubstituted" or "substituted" in the case of polysubstitution is to be understood as meaning that the substitution is both on different and on the same atoms several times with identical or different substituents, for example three times on the same C atom as in the case of $CF_3$, or at different places as in the case of —CH(OH)—CH=CH—$CHCl_2$. Particularly preferred substituents are F, Cl and OH. In respect of cycloalkyl, the hydrogen radical can also be replaced by $OC_{1-3}$-alkyl or $C_{1-3}$-alkyl (in each case mono- or polysubstituted or unsubstituted), in particular methyl, ethyl, n-propyl, i-propyl, $CF_3$, methoxy or ethoxy.

The term $(CH_2)_{3-6}$ is to be understood as meaning —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and —$CH_2$—$CH_2$—$CH_2$—$CH_2$—$CH_2$—$CH_2$—, $(CH_2)_{1-4}$ is to be understood as meaning —$CH_2$—, —$CH_2$—$CH_2$—, —$CH_2$—$CH_2$—$CH_2$— and —$CH_2$—$CH_2$—$CH_2$—$CH_2$—, $(CH_2)_{4-5}$ is to be understood as meaning —$CH_2$—$CH_2$—$CH_2$—$CH_2$— and —$CH_2$—$CH_2$—$CH_2$—$CH_2$—$CH_2$— etc.

An aryl radical is also understood as meaning ring systems having at least one aromatic ring but without heteroatoms in even only one of the rings. Examples are phenyl, naphthyl, fluoranthenyl, fluorenyl, tetralinyl or indanyl, in particular 9H-fluorenyl or anthracenyl radicals, which can be unsubstituted or mono- or polysubstituted.

A heteroaryl radical is also understood as meaning heterocyclic ring systems having at least one unsaturated ring which contain one or more heteroatoms from the group consisting of nitrogen, oxygen and/or sulfur and can also be mono- or polysubstituted. Examples which may be listed from the group of heteroaryls are furan, benzofuran, thiophene, benzothiophene, pyrrole, pyridine, pyrimidine, pyrazine, quinoline, isoquinoline, phthalazine, benzo-1,2,5-thiadiazole, benzothiazole, indole, benzotriazole, benzodioxolane, benzodioxane, carbazole, indole and quinazoline.

In connection with aryl and heteroaryl, substituted is also understood as meaning substitution of the aryl or heteroaryl by $R^{23}$, $OR^{23}$, a halogen, preferably F and/or Cl, a $CF_3$, a CN, an $NO_2$, an $NR^{24}R^{25}$, a $C_{1-6}$-alkyl (saturated), a $C_{1-6}$-alkoxy, a $C_{3-8}$-cycloalkoxy, a $C_{3-8}$-cycloalkyl or a $C_{2-6}$-alkylene.

In this context, the radical $R^{23}$ represents H, a $C_{1-10}$-alkyl, preferably a $C_{1-6}$-alkyl, an aryl or heteroaryl radical or an aryl or heteroaryl radical which is bonded via a $C_{1-3}$-alkylene group, wherein these aryl and heteroaryl radicals may not themselves be substituted by aryl or heteroaryl radicals.

The radicals $R^{24}$ and $R^{25}$, which are identical or different, represent H, a $C_{1-10}$-alkyl, preferably a $C_{1-6}$-alkyl, an aryl or a heteroaryl radical or an aryl or heteroaryl radical which is bonded via a $C_{1-3}$-alkylene group, wherein these aryl and heteroaryl radicals may not themselves be substituted by aryl or heteroaryl radicals. Alternatively, the radicals $R^{24}$ and $R^{25}$ may together denote $CH_2CH_2OCH_2CH_2$, $CH_2CH_2NR^{26}CH_2CH_2$ or $(CH_2)_{3-6}$.

The radical $R^{26}$ represents H, a $C_{1-10}$-alkyl, preferably a $C_{1-6}$-alkyl, an aryl or heteroaryl radical or an aryl or heteroaryl radical which is bonded via a $C_{1-3}$-alkylene group, wherein these aryl and heteroaryl radicals may not themselves be substituted by aryl or heteroaryl radicals.

In the context of this invention, the term salt is to be understood as meaning any form of the active compound according to the invention in which this assumes an ionic form or is charged and is coupled with a counter-ion (a cation or anion) or is in solution. The term salt is also to be understood as including complexes of the active compound with other molecules and ions, in particular complexes which are complexed via ionic interactions.

In the context of this invention, the term of physiologically acceptable salt (in particular with cations or bases) is understood as meaning salts of at least one of the compounds according to the invention—usually of a (deprotonated) acid—as the anion with at least one, preferably inorganic cation, which are physiologically acceptable—especially when used in humans and/or mammals. The salts of the alkali metals and alkaline earth metals and also with $NH_4^+$ are particularly preferred, but especially (mono-) or (di-) sodium, (mono-) or (di-)potassium, magnesium or calcium salts.

In the context of this invention, the term of physiologically acceptable salt (in particular with anions or acids) is furthermore understood as meaning salts of at least one of the compounds according to the invention—usually protonated, for example on the nitrogen—as the cation with at least one anion, which are physiologically acceptable—especially when used in humans and/or mammals. In particular, in the context of the invention this is understood as meaning the salt formed with a physiologically acceptable acid, namely salts of the particular active compound with inorganic or organic acids which are physiologically acceptable—especially when used in humans and/or mammals. Examples of physiologically acceptable salts of particular acids include salts of hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid, citric acid, glutamic acid, 1,1-dioxo- 1,2-dihydro1b6-benzo[d]isothiazol-3-one (saccharic acid), monomethylsebacic acid, 5-oxo-proline, hexane-1-sulfonic acid, nicotinic acid, 2-, 3- or 4-aminobenzoic acid, 2,4,6-trimethyl-benzoic acid, α-liponic acid, acetylglycine, acetylsalicylic acid, hippuric acid and/or aspartic acid. The hydrochloride salt is particularly preferred.

In the context of this invention and in each use described and each of the pharmaceutical compositions described, suitable salts are salts of the particular active compound with inorganic or organic acids and/or a sugar substitute, such as saccharine, cyclamate or acesulfame. However, the hydrochloride is particularly preferred.

Other preferred embodiments of the C-imidazo[1,2-a]pyridin-3-yl-methylamine compounds according to the invention are described hereinafter.

The preparation of the substituted C-imidazo[1,2-a]pyridin-3-yl-methylamine compounds corresponding to formula I can be carried out by conventional methods known those skilled in the art of chemical synthesis.

Preferably, the preparation of the compounds of formula I according to the invention is carried out stepwise, in the first step by reaction of a substituted 2-aminopyridine of formula III, wherein $R^1$ and $R^2$ have the meanings given above

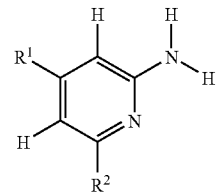

preferably in solution, with an o-halocarbonyl compound corresponding to formula IV

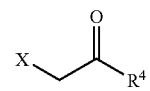

wherein the radicals $R^3$ and $R^4$ have the meanings given above and X represents halogen, preferably Cl, Br or I, with elimination of water and hydrogen halide and formation of the intermediate corresponding to formula V

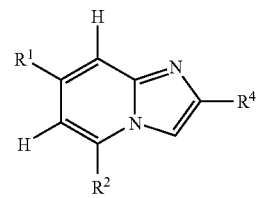

and subsequent aminomethylation of this intermediate V in a second step.

The first process step is advantageously carried out under conditions under which water and/or hydrogen halide are preferably removed continuously from the reaction mixture. Hydrogen halide can preferably be bound by addition of soluble or insoluble organic or inorganic bases and removed from the reaction mixture in this way. Water can preferably be removed from the reaction mixture by azeotropic distillation or by addition of desiccants or hygroscopic substances.

The preparation of the intermediates corresponding to formula V according to the invention by the above process, with or without a solvent, at temperatures of more than 100° C. is a further possibility for removing water from the reaction mixture.

The preparation of the intermediates of formula V according to the invention by reaction of substituted 2-aminopyridines of formula III with α-halocarbonyl compounds of formula IV wherein X represents Br in boiling anhydrous ethanol is particularly preferred.

The preparation of the intermediates of formula V according to the invention by reaction of substituted 2-aminopyridines of formula III with α-halocarbonyl compounds of formula IV wherein X represents Br or Cl in boiling anhydrous methylene chloride and/or trichloromethane using a water separator is also preferred.

The substituted 2-aminopyridines of formula III and the α-halocarbonyl compounds of formula IV are generally commercially available or can be prepared by conventional methods known to persons skilled in the art of chemical synthesis.

The second process step is the aminomethylation of the intermediates of formula V according to the invention by reaction with imminium salts of the formula VI, which can be prepared either separately beforehand or in situ.

The imminium salts of formula VI

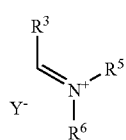

wherein Y preferably denotes Cl—, AlCl$_4$—, Br— or I—, can be prepared by processes known from the literature by reacting aminals of formula VII

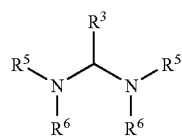

with acid chlorides, for example acetyl chloride or thionyl chloride (Houben-Weyl—Methoden der organischen Chemie [Methods of Organic Chemistry], E21b, 1995, p. 1925-1929).

The imminium salts of formula VI do not have to be isolated here, but can be reacted in situ with intermediates of formula V according to the invention to give substances of formula I according to the invention.

The reaction of intermediates of formula V according to the invention with paraformaldehyde and dimethylammonium chloride at temperatures of between 50 and 150° C. is moreover a suitable process for the introduction of a dimethylaminomethyl radical.

After the process employed for their preparation, the substituted C-imidazo[1,2-a]pyridin-3-yl-methylamines of formula I according to the invention can be isolated either as a free base or as a salt. The free base of the particular compound of formula I is conventionally obtained after the reaction according to the process according to the invention described above has been carried out and optionally subsequent working up by conventional methods known to persons skilled in the art. The free base, obtained in this way or formed in situ without isolation, of the particular compound of formula I can then be converted, for example by reaction with an inorganic or organic acid, preferably with hydrochloric acid, hydrobromic acid, sulfuric acid, phosphoric acid, methanesulfonic acid, p-toluenesulfonic acid, carbonic acid, formic acid, acetic acid, oxalic acid, succinic acid, tartaric acid, mandelic acid, fumaric acid, lactic acid, citric acid, glutamic acid or aspartic acid, into the corresponding physiologically acceptable salt.

The conversion of the particular compound of formula I can preferably also be achieved by addition of trimethylsilyl chloride (TMSCl) to the compound of formula I as the free base dissolved in a suitable organic solvent, such as e.g. butan-2-one (methyl ethyl ketone).

If the substituted C-imidazo[1,2-a]pyridin-3-yl-methylamines of formula I according to the invention are obtained in the form of their racemates or other mixtures of their various enantiomers and/or diastereomers by the preparation process according to the invention, these can be separated and optionally isolated by conventional processes known to persons skilled in the art. Suitable processes include, for example, chromatographic separation processes and fractional crystallization processes. Particularly preferred chromatographic separation processes are liquid chromatography processes under normal pressure or under increased pressure, preferably MPLC and HPLC processes. In the aforementioned separation processes individual enantiomers, e.g. diastereomeric salts formed by HPLC on a chiral phase or by crystallization with chiral acids, for example (+)-tartaric acid, (−)-tartaric acid or (+)-10-camphorsulfonic acid, can be separated from one another.

The present invention also relates to the use of at least one substituted C-imidazo[1,2-a]pyridin-3-yl-methylamine of formula I given above as an inhibitor of nitrogen monoxide synthase in pharmaceutical compositions for the treatment of conditions in which NO synthase is implicated, e.g., migraine, septic shock, neurodegenerative diseases, such as multiple sclerosis, Parkinson's disease, Alzheimer's disease or Huntington's disease, inflammatory pain, cerebral ischaemia, diabetes, meningitis, arteriosclerosis or cancer diseases or for wound healing.

The pharmaceutical compositions of the invention can be in the form of liquid, semi-solid or solid medicament forms, for example in the form of injection solutions, drops, juices, syrups, sprays, suspensions, granules, tablets, patches, capsules, plasters, suppositories, ointments, creams, lotions, gels, emulsions, aerosols or in a multiparticulate form, for example in the form of pellets or granules, and can also be administered as such.

In addition to at least one substituted C-imidazo[1,2-a]pyridin-3-yl-methylamine of formula I according to the invention, the pharmaceutical compositions of the invention typically comprise further physiologically acceptable pharmaceutical auxiliaries, which are preferably selected from the group consisting of carrier materials, fillers, solvents, diluents, surface-active substances, dyestuffs, preservatives, disintegrating agents, slip agents, lubricants, flavorings and binders. The choice of the physiologically acceptable auxiliary substances and the amounts thereof to be employed depend on whether the medicament is to be administered orally, subcutaneously, parenterally, intravenously, intraperitoneally, intradermally, intramuscularly, intranasally, buccally, rectally or locally, for example on infections on the skin, the mucous membranes and on the eyes. Formulations in the form of tablets, coated tablets, capsules, granules, pellets, drops, juices and syrups are preferably suitable for oral administration, and solutions, suspensions, easily reconstitutable dry formulations and sprays are suitable for parenteral, topical and inhalatory administration. Compounds of formula I according to the invention in a depot in dissolved form or in a plaster, optionally with the addition of agents which promote penetration through the skin, are suitable formulations for percutaneous administration. Formulation forms which can be used orally or percutaneously can also release the compounds of formula I according to the invention in a delayed manner.

The pharmaceutical compositions are prepared using conventional agents, devices, methods and process known to persons skilled in the art, such as are described, for example, in "Remington's Pharmaceutical Sciences", ed. A. R. Gennaro, 17th ed., Mack Publishing Company, Easton, Pa. (1985), in particular in part 8, section 76 to 93. The corresponding description in the literature is incorporated herein by reference as part of this disclosure.

The amount of the particular compound of formula I to be administered to the patient can vary and depends, for example, on the weight or the age of the patient and on the mode of administration, the indication and the severity of the disease. 0.1 to 5,000 mg/kg, preferably 1 to 500 mg/kg, particularly preferably 2 to 250 mg per kg of body weight of the patient of at least one compound of formula I are conventionally administered.

The invention is illustrated in further detail hereinafter with reference to examples, which are merely exemplary and are not intended to be limiting.

EXAMPLES

Example 1

Synthesis of 2,7-dimethyl-imidazo[1,2-α]pyridin-3-ylmethyl)-dimethyl-amine

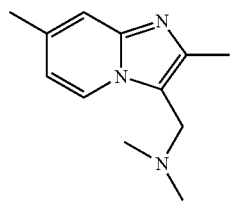

2,7-Dimethyl-imidazo[1,2-α]pyridin-3-ylmethyl)-dimethyl-amine 1.50 g of 2,7-dimethyl-imidazo[1,2-α]pyridine were added to 0.83 g formaldehyde (formalin 37% strength) and 1.30 ml dimethylamine (40% strength in water) in 1.41 ml glacial acetic acid at 0° C. under a nitrogen atmosphere, and the reaction mixture was heated at 50° C. for two hours and stirred overnight at a temperature of 20 to 25° C. For further purification, the reaction mixture was rendered alkaline with 10% strength sodium hydroxide solution and extracted with diethyl ether. The organic phases were combined and dried over sodium sulfate. After removal of the organic solvent by distillation, 1.70 g of the crude product were obtained. After purification by column chromatography, 177 mg of the product were obtained as a colorless oil. 177 mg of the base were diluted with 1 ml of methyl ethyl ketone and precipitated as the hydrochloride by addition of 0.009 ml water and 0.121 ml chlorotrimethylsilane and subsequent stirring overnight. 170 mg 2,7-dimethyl-imidazo[1,2-α]pyridin-3-ylmethyl)-dimethyl-amine hydrochloride (corresponds to 6.5% of the theoretical amount) were obtained as a colorless solid.

Example 2

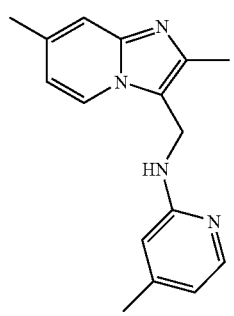

(2,7-Dimethyl-imidazo[1,2-a]pyridin-3-ylmethyl)-(4-methyl-pyridin-2-yl)-amine

1st Stage: Synthesis of 2,7-dimethyl-imidazo[1,2-a]pyridine-3-carboxylic acid ethyl ester 15.2 g ethyl 2-chloroacetate were added to a solution of 10 g 2-amino-4-methylpyridine in 200 ml ethanol, the mixture was stirred under reflux for 8 hours and the reaction solution was stirred overnight at room temperature. After removal of the solvent, the residue was taken up with aqueous 10% strength HCl, and the mixture was washed with methylene chloride, rendered basic with sodium bicarbonate and extracted with methylene chloride. The combined organic phases were washed with water and dried over sodium sulfate. After removal of the solvent and purification by column chromatography, the product was obtained in a yield of 35%.

2nd Stage: Synthesis of 2,7-dimethyl-imidazo[1,2-a]pyridine-3-carboxylic acid (4-methyl-pyridin-2-yl)-amide 37 ml n-BuLi (1.6 M in hexane) were added dropwise to a solution of 3.2 g 2-amino-4-methylpyridine in 57 ml tetrahydrofuran (THF) at 0° C., while stirring. After warming to room temperature, the mixture was stirred for one hour. The reaction solution was cooled to −78° C., 5.8 g 2,7-dimethylimidazo[1,2-a]pyridine-3-carboxylic acid ethyl ester, dissolved in 10 ml THF, were slowly added dropwise, and the mixture was stirred for one hour. After addition of 60 ml ammonium chloride at room temperature, the mixture was extracted with methylene chloride, the organic phases were dried over sodium sulfate, and the solvent was removed. The product was purified by boiling and precipitation in hexane and was obtained with a yield of 68%.

3rd Stage: Synthesis of (2,7-dimethyl-imidazo[1,2-a]pyridin-3-ylmethyl)-(4-methyl-pyridin-2-yl)-amine 760 mg 2,7-dimethyl-imidazo[1,2-a]pyridine-3-carboxylic acid (4-methyl-pyridin-2-yl)-amide were added to a suspension of 160 mg lithium aluminium hydride in 12 ml tetrahydrofuran at room temperature. The mixture was then heated under reflux for 2.5 hours. After addition of an aqueous KOH solution, the resulting suspension was heated under reflux again for 15 minutes. After filtration, distillation of the solvent and purification by column chromatography, the product was obtained with a yield of 25%.

Molecular Pharmacology Investigation:

The IC50 value of each of the example compounds as an inhibitor of NO synthase was determined in a citrulline assay. This assay was carried out as described by D. S. Bredt and S. H. Snyder (Proc. Natl. Acad. Sci. USA (1990), 87, 682-685). The results of example compounds in the citrulline assay are reproduced in the following Table.

TABLE

| Example no.: | Inhibition of nitrogen monoxide synthase IC50 [μm] |
|---|---|
| 1 | 4.0 |
| 2 | 2.5 |

The test results show that the compounds of the invention are effective inhibitors of NO synthase.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:
1. A substituted C-imidazo[1,2-a]pyridin-3-yl-methylamine compound corresponding to formula I

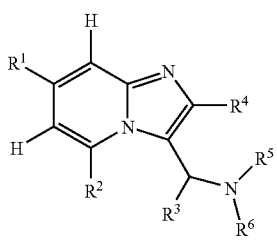

wherein
R$^1$ represents OH, SH, NH$_2$, NHCH$_3$, N(CH$_3$)$_2$, CH$_3$, CH$_2$Cl, CH$_2$F, CHF$_2$, CF$_3$, OCH$_3$, OCH$_2$Cl, OCH$_2$F, OCHF$_2$, OCF$_3$, C$_2$H$_5$, CHClCH$_3$, CH$_2$CH$_2$Cl, CHFCH$_3$, CH$_2$CH$_2$F, CH$_2$CHF$_2$, CH$_2$CF$_3$, OC$_2$H$_5$, COOH, CH$_2$OH, CHOHCH$_3$ or CH$_2$CH$_2$OH, R$^2$ represents H or CH$_3$, R$^3$ represents H;

R$^4$ represents H; or
an alkyl radical selected from the group consisting of methyl, ethyl, 1-methylethyl, 1,1-dimethylethyl, propyl, 2-methylpropyl, 1-methylpropyl, 1-ethylpropyl, butyl, i-butyl, n-butyl, tert-butyl, 1-methylbutyl, 2-methylbutyl, 3-methylbutyl, 2,2-dimethylbutyl, pentyl, 2-methylpentyl, 3-methylpentyl, 1,1-dimethylethyl, 1,2-dimethylpropyl, 2,2-dimethylpropyl, 1-ethylpropyl, hexyl, heptyl, octyl, nonyl, decyl, undecyl and dodecyl; wherein said alkyl radical is unsubstituted or mono- or polysubstituted by a substituent selected from the group consisting of F, Cl, Br, I, NH$_2$, SH and OH; or
a cyclic radical selected from the group consisting of cyclopropyl, cyclobutyl, cyclopentyl, cyclohexyl, cycloheptyl, cyclooctyl, cyclopentenyl, cyclohexenyl, cycloheptenyl and cyclooctenyl, wherein said cyclic radical is unsubstituted or mono- or polysubstituted by a substituent selected from the group consisting of methyl, ethyl, n-propyl, i-propyl, CF$_3$, methoxy and ethoxy; or
a radical corresponding to formula II

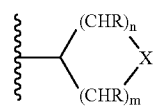

wherein n represents a number from 0 to 6,
m represents a number from 0 to 6,
$1 \leq m+n \leq 6$
X represents O, S, SO, SO$_2$ or NR$_7$, and each R independently represents H, F, Br, I, Cl, OH, SH, NH$_2$, NO$_2$, CH$_3$, C$_2$H$_5$, OCH$_3$, OC$_2$H$_5$, or OCF$_3$;

R$^5$ represents H; an alkyl radical selected from the group consisting of methyl, ethyl, 1-methylethyl, 1,1-dimethylethyl, propyl, 2-methylpropyl, 1-methylpropyl, 1-ethylpropyl, butyl, i-butyl, n-butyl, tert-butyl, 1-methylbutyl, 2-methylbutyl, 3-methylbutyl, 2,2-dimethylbutyl, pentyl, 2-methylpentyl, 3-methylpentyl, 1,1-dimethylpropyl, 1,2-dimethylpropyl, 2,2-dimethylpropyl, 1-ethylpropyl and hexyl, wherein said alkyl radical is unsubstituted or mono- or polysubstituted by a substituent selected from the group consisting of F, Cl, Br, I, NH$_2$, SH and OH; or a cyclic radical selected from the group consisting of cyclopropyl, cyclobutyl, cyclopentyl, cyclohexyl, cycloheptyl, cyclooctyl, cyclopentenyl, cyclohexenyl, cycloheptenyl and cyclooctenyl, wherein said cyclic radical is unsubstituted or mono- or polysubstituted by a substituent selected from the group consisting of methyl, ethyl, n-propyl, i-propyl, CF$_3$, methoxy and ethoxy;

R$^6$ represents H; an alkyl radical selected from the group consisting of methyl, ethyl, 1-methylethyl, 1,1-dimethylethyl, propyl, 2-methylpropyl, 1-methylpropyl, 1-ethylpropyl, butyl, i-butyl, n-butyl, tert-butyl, 1-methylbutyl, 2-methylbutyl, 3-methylbutyl, 2,2-dimethylbutyl, pentyl, 2-methylpentyl, 3-methylpentyl, 1,1-dimethylpropyl, 1,2-dimethylpropyl, 2,2-dimethylpropyl, 1-ethylpropyl and hexyl; wherein said alkyl radical is unsubstituted or mono- or polysubstituted by a substituent selected from the group consisting of F, Cl, Br, I, NH$_2$, SH and OH; or a cyclic radical selected from the group consisting of cyclopropyl, cyclobutyl, cyclopentyl, cyclohexyl, cycloheptyl, cyclooctyl, cyclopentenyl, cyclohexenyl, cycloheptenyl and cyclooctenyl, wherein said cyclic radical is unsubstituted or mono- or polysubstituted by a substituent selected from the group consisting of methyl, ethyl, n-propyl, i-propyl, CF$_3$, methoxy and ethoxy; or a radical corresponding to formula IIa

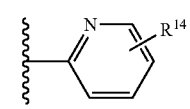

or the radicals R$^5$ and R$^6$ together form a ring and denote CH$_2$CH$_2$OCH$_2$CH$_2$, CH$_2$CH$_2$NR11CH$_2$CH$_2$ or (CH$_2$)$_{3-6}$, R$^7$ represents H; or an alkyl radical selected from the group consisting of methyl, ethyl, propyl, 1-methylethyl, butyl, 1-methylpropyl, 2-methylpropyl, 1,1-dimethylethyl, pentyl, 1,1-dimethylethyl, 1,2-dimethylpropyl, 2,2-dimethylpropyl, 1-ethylpropyl and hexyl; or a cyclic radical selected from the group consisting of cyclopropyl, 2-methylcyclopropyl, cyclopropylmethyl, cyclobutyl, 2-methylcyclobutyl, 3-methylcyclobutyl, cyclobutylmethyl, cyclopentyl, cyclohexyl, and cyclooctyl; or an acyl radical C(O)R8 or a sulfonyl radical S(O$_2$)R9, R$^8$ represents H; or an unsubstituted alkyl radical selected from the group consisting of methyl, ethyl, propyl, 1-methylethyl, butyl, 1-methylpropyl, 2-methylpropyl, 1,1-dimethylethyl, pentyl, 1,1-dimethylethyl, 1,2-dimethylpropyl, 2,2-dimethylpropyl, hexyl, and 1-methylpentyl; or an aryl radical selected from the group consisting of phenyl, 3-hydroxyphenyl, 3-methoxyphenyl, 2,3-dihydroxyphenyl, 2,3-dimethoxyphenyl and 1-naphthyl;

$R^9$ represents H; or an unsubstituted alkyl radical selected from the group consisting of methyl, ethyl, propyl, methylethyl, butyl, 1-methylpropyl, 2-methylpropyl, 1,1-dimethylethyl, pentyl, 1,1-dimethylethyl, 1,2-dimethylpropyl, 2,2-dimethylpropyl, hexyl, and 1-methylpentyl; or an aryl radical selected from the group consisting of phenyl, 3-hydroxyphenyl, 3-methoxyphenyl, 2,3-dihydroxyphenyl, 2,3-dimethoxyphenyl and 1-naphthyl;

$R^{11}$ represents H; or an unsubstituted alkyl radical selected from the group consisting of methyl, ethyl, propyl, I-methylethyl, butyl, I-methylpropyl, 2-methylpropyl, 1,1-dimethylethyl, pentyl, 1,1-dimethylpropyl, 1,2-dimethylpropyl, 2,2-dimethylpropyl, hexyl, and 1-methylpentyl; or an unsubstituted cycloalkyl radical selected from the group consisting of cyclopropyl, cyclobutyl, cyclopentyl, cyclohexyl, cycloheptyl, cyclooctyl, cyclopentenyl, cyclohexenyl, cycloheptenyl and cyclooctenyl; or an aryl radical selected from the group consisting of phenyl, 3-hydroxyphenyl, 3-methoxyphenyl, 2,3-dihydroxyphenyl, 2,3-dimethoxyphenyl and 1-naphthyl; or an unsubstituted heteroaryl radical selected from the group consisting of pyrrolyl, furyl, thienyl, pyrazolyl, imidazolyl, pyridinyl, pyridazinyl, pyrimidinyl, pyrazinyl, pyranyl, indolyl, indazolyl, purinyl, pyrimidinyl, indolizinyl, quinolinyl, isoquinolinyl, quinazolinyl, carbazolyl, phenazinyl and phenothiazinyl; or an aryl radical which is bonded via $C_{1-3}$-alkylene and is selected from the group consisting of phenyl, 3-hydroxyphenyl, 3-methoxyphenyl, 2,3-dihydroxyphenyl, 2,3-dimethoxyphenyl and 1-naphthyl; or an unsubstituted heteroaryl radical which is bonded via $C_{1,3}$-alkylene and is selected from the group consisting of pyrrolyl, furyl, thienyl, pyrazolyl, imidazolyl, pyridinyl, pyridazinyl, pyrimidinyl, pyrazinyl, pyranyl, indolyl, indazolyl, purinyl, pyrimidinyl, indolizinyl, quinolinyl, isoquinolinyl, quinazolinyl, carbazolyl, phenazinyl and phenothiazinyl; or an acyl radical $C(O)R^{12}$; or a sulfonyl radical $S(O_2)R^{13}$;

$R^{12}$ represents H; or an unsubstituted alkyl radical selected from the group consisting of methyl, ethyl, propyl, 1-methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, and 1-methylpentyl; or an aryl radical selected from the group consisting of phenyl, 3-hydroxyphenyl, 3-methoxyphenyl, 2,3-dihydroxyphenyl, 2,3-dimethoxyphenyl and 1-naphthyl;

$R^{13}$ represents H; an unsubstituted alkyl radical selected from the group consisting of methyl, ethyl, propyl, 1-methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, and 1-methylpentyl; or an aryl radical selected from the group consisting of phenyl, 3-hydroxyphenyl, 3-methoxyphenyl, 2,3-dihydroxyphenyl, 2,3-dimethoxyphenyl and 1-naphthyl; and $R^{14}$ represents H, F, Br, I, Cl, OH, SH, $NH_2$, $NO_2$, $CH_3$, $C_2H_5$, $OCH_3$, $OC_2H_5$, or $OCF_3$;

or a pharmaceutically acceptable salt thereof, with the proviso that the following compounds:

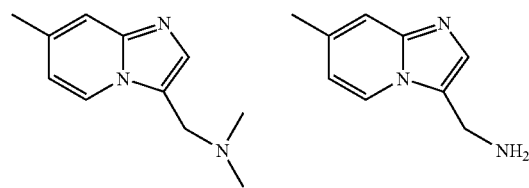

are excluded.

2. A compound according to claim 1, wherein said compound contains at least one asymmetric center and is present in the form of a racemic mixture.

3. A compound according to claim 1, wherein said compound contains at least one asymmetric center and is present in the form of a pure stereoisomer.

4. A compound according to claim 1, wherein said compound contains at least one asymmetric center and is present in the form of a mixture of enantiomers or a mixture of diastereomers.

5. A compound according to claim 1, wherein $R^4$ represents:

an alkyl radical selected from the group consisting of methyl, ethyl, 1-methylethyl, 1,1-dimethylethyl, propyl, 2-methylpropyl, 1-methylpropyl, 1-ethylpropyl, butyl, i-butyl, n-butyl, tert-butyl, 1-methylbutyl, 2-methylbutyl, 3-methylbutyl, 2,2-dimethylbutyl, pentyl, 2-methylpentyl, 3-methylpentyl, 1,1-dimethylethyl, 1,2-dimethylpropyl, 2,2-dimethylpropyl, 1-ethylpropyl, hexyl, heptyl, octyl, nonyl, decyl, undecyl and dodecyl; wherein said alkyl radical is unsubstituted or mono- or polysubstituted by a substituent selected from the group consisting of F, Cl, Br, I, $NH_2$, SH and OH; or a cyclic radical selected from the group consisting of cyclopropyl, cyclobutyl, cyclopentyl, cyclohexyl, cycloheptyl, cyclooctyl, cyclopentenyl, cyclohexenyl, cycloheptenyl and cyclooctenyl, wherein said cyclic radical is unsubstituted or mono- or polysubstituted by a substituent selected from the group consisting of methyl, ethyl, n-propyl, i-propyl, $CF_3$, methoxy and ethoxy; or a radical corresponding to formula II

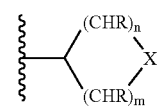

wherein n represents a number from 0 to 6, m represents a number from 0 to 6, $1 \leq m+n \leq 6$, X represents O, S, SO, $SO_2$ or $NR_7$, and each R independently represents H, F, Br, I, Cl, OH, SH, $NH_2$, $NO_2$, $CH_3$, $C_2H_5$, $OCH_3$, $OC_2H_5$, or $OCF_3$.

6. A compound according to claim 1, wherein $R^1$ represents $C_2H_5$, $CH_3$ or $CF_3$.

7. A compound according to claim 6, wherein $R^1$ represents $CH_3$.

8. A compound according to claim 1, wherein $R^5$ represents H or an alkyl radical selected from the group consisting of methyl, ethyl, 1-methylethyl, 1,1-dimethylethyl, propyl, 2-methylpropyl, 1-methylpropyl, 1-ethylpropyl, butyl, i-butyl, n-butyl, tert-butyl, 1-methylbutyl, 2-methylbutyl, 3-methylbutyl, 2,2-dimethylbutyl, pentyl, 2-methylpentyl, 3-methylpentyl, 1,1-dimethylpropyl, 1,2-dimethylpropyl, 2,2-dimethylpropyl, 1-ethylpropyl and hexyl, wherein said alkyl radical is unsubstituted or mono- or polysubstituted by a substituent selected from the group consisting of F, Cl, Br, I, $NH_2$, SH and OH.

9. A compound according to claim 1, wherein $R^2$ represents H.

10. A compound according to claim 1, selected from the group consisting of 2,7-dimethyl-imidazo [1,2-a]pyridin-3-ylmethyl)-dimethyl-amine, and (2,7-dimethyl-imidazo [1,2-a]pyridin-3-ylmethyl)-4-methyl-pyridin-2-yl)-amine.

11. A composition comprising a compound according to claim 1, and at least one physiologically acceptable pharmaceutical auxiliary substance.

12. A method of treating in a patient in need thereof, said method comprising administering to said patient a pharmaceutically effective amount of a compound according to claim 1.

13. A method of inhibiting nitrogen monoxide synthase activity in an organism, said method comprising administering to said organism an effective nitrogen monoxide synthase inhibiting amount of a compound according to claim 1.

14. A substituted C-imidazo [1,2-a]pyridin-3-yl-methylamine compound corresponding to formula I

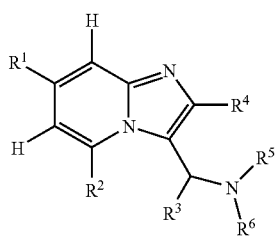

wherein
$R^1$ represents OH, SH, $NH_2$, $NHCH_3$, $N(CH_3)_2$, $CH_3$, $CH_2Cl$, $CH_2F$, $CHF_2$, $CF_3$, $OCH_3$, $OCH_2Cl$, $OCH_2F$, $OCHF_2$, $OCF_3$, $C_2H_5$, $CHClCH_3$, $CH_2CH_2Cl$, $CHFCH_3$, $CH_2CH_2F$, $CH_2CHF_2$, $CH_2CF_3$, $OC_2H_5$, COOH, $CH_2OH$, $CHOHCH_3$ or $CH_2CH_2OH$,
$R^2$ represents H or $CH_3$,
$R^3$ represents H;
$R^4$ represents H; or
an alkyl radical selected from the group consisting of methyl, ethyl, 1-methylethyl, 1,1-dimethylethyl, propyl, 2-methylpropyl, 1-methylpropyl, 1-ethylpropyl, butyl, i-butyl, n-butyl, tert-butyl, 1-methylbutyl, 2-methylbutyl, 3-methylbutyl, 2,2-dimethylbutyl, pentyl, 2-methylpentyl, 3-methylpentyl, 1,1-dimethylethyl, 1,2-dimethylpropyl, 2,2-dimethylpropyl, 1-ethylpropyl, hexyl, heptyl, octyl, nonyl, decyl, undecyl and dodecyl; wherein said alkyl radical is unsubstituted or mono- or polysubstituted by a substituent selected from the group consisting of F, Cl, Br, I, $NH_2$, SH and OH; or
a cyclic radical selected from the group consisting of cyclopropyl, cyclobutyl, cyclopentyl, cyclohexyl, cycloheptyl, cyclooctyl, cyclopentenyl, cyclohexenyl, cycloheptenyl and cyclooctenyl, wherein said cyclic radical is unsubstituted or mono- or polysubstituted by a substituent selected from the group consisting of methyl, ethyl, n-propyl, i-propyl, $CF_3$, methoxy and ethoxy; or
a radical corresponding to formula II

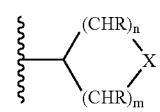

wherein n represents a number from 0 to 6,
m represents a number from 0 to 6,
$1 \leq m+n \leq 6$
X represents O, S, SO, $SO_2$ or $NR_7$, and
each R independently represents H, F, Br, I, Cl, OH, SH, $NH_2$, $NO_2$, $CH_3$, $C_2H_5$, $OCH_3$, $OC_2H_5$, or $OCF_3$;
$R^5$ represents H; an alkyl radical selected from the group consisting of methyl, ethyl, 1-methylethyl, 1,1-dimethylethyl, propyl, 2-methylpropyl, 1-methylpropyl, 1-ethylpropyl, butyl, i-butyl, n-butyl, tert-butyl, 1-methylbutyl, 2-methylbutyl, 3-methylbutyl, 2,2-dimethylbutyl, pentyl, 2-methylpentyl, 3-methylpentyl, 1,1-dimethylpropyl, 1,2-dimethylpropyl, 2,2-dimethylpropyl, 1-ethylpropyl and hexyl, wherein said alkyl radical is unsubstituted or mono- or polysubstituted by a substituent selected from the group consisting of F, Cl, Br, I, $NH_2$, SH and OH; or a cyclic radical selected from the group consisting of cyclopropyl, cyclobutyl, cyclopentyl, cyclohexyl, cycloheptyl, cyclooctyl, cyclopentenyl, cyclohexenyl, cycloheptenyl and cyclooctenyl, wherein said cyclic radical is unsubstituted or mono- or polysubstituted by a substituent selected from the group consisting of methyl, ethyl, n-propyl, i-propyl, $CF_3$, methoxy and ethoxy;
$R^6$ represents H; an alkyl radical selected from the group consisting of methyl, ethyl, 1-methylethyl, 1,1-dimethylethyl, propyl, 2-methylpropyl, 1-methylpropyl, 1-ethylpropyl, butyl, i-butyl, n-butyl, tert-butyl, 1-methylbutyl, 2-methylbutyl, 3-methylbutyl, 2,2-dimethylbutyl, pentyl, 2-methylpentyl, 3-methylpentyl, 1,1-dimethylpropyl, 1,2-dimethylpropyl, 2,2-dimethylpropyl, 1-ethylpropyl and hexyl; wherein said alkyl radical is unsubstituted or mono- or polysubstituted by a substituent selected from the group consisting of F, Cl, Br, I, $NH_2$, SH and OH; or a cyclic radical selected from the group consisting of cyclopropyl, cyclobutyl, cyclopentyl, cyclohexyl, cycloheptyl, cyclooctyl, cyclopentenyl, cyclohexenyl, cycloheptenyl and cyclooctenyl, wherein said cyclic radical is unsubstituted or mono- or polysubstituted by a substituent selected from the group consisting of methyl, ethyl, n-propyl, i-propyl, $CF_3$, methoxy and ethoxy; or
a radical corresponding to formula IIa

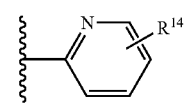

or the radicals $R^5$ and $R^6$ together form a ring and denote $CH_2CH_2OCH_2CH_2$, $CH_2CH_2NR_{11}CH_2CH_2$ or $(CH_2)_{3-6}$, $R^7$ represents H; or an alkyl radical selected from the group consisting of methyl, ethyl, propyl, 1-methylethyl, butyl, 1-methylpropyl, 2-methylpropyl, 1,1-dimethylethyl, pentyl, 1,1-dimethylethyl, 1,2-dimethylpropyl, 2,2-dimethylpropyl, 1-ethylpropyl and hexyl; or a cyclic radical selected from the group consisting of cyclopropyl, 2-methylcyclopropyl, cyclopropylmethyl, cyclobutyl, 2-methylcyclobutyl, 3-methylcyclobutyl, cyclobutylmethyl, cyclopentyl, cyclohexyl, and cyclooctyl; or an acyl radical C(O)R8 or a sulfonyl radical $S(O_2)R9$, $R^8$ represents H; or an unsubstituted alkyl radical selected from the group consisting of methyl, ethyl, propyl, 1-methylethyl, butyl, 1-methylpropyl, 2-methylpropyl, 1,1-dimethylethyl, pentyl, 1,1-dimethylethyl, 1,2-dimethylpropyl, 2,2-dimethylpropyl, hexyl, and 1-methylpentyl; or an aryl radical selected from the group consisting of phenyl, 3-hydroxyphenyl, 3-methoxyphenyl, 2,3-dihydroxyphenyl, 2,3-dimethoxyphenyl and 1-naphthyl;

$R^9$ represents H; or an unsubstituted alkyl radical selected from the group consisting of methyl, ethyl, propyl, methylethyl, butyl, 1-methylpropyl, 2-methylpropyl, 1,1-dimethylethyl, pentyl, 1,1-dimethylethyl, 1,2-dimethylpropyl, 2,2-dimethylpropyl, hexyl, and 1-methylpentyl; or an aryl radical selected from the group consisting of phenyl, 3-hydroxyphenyl, 3-methoxyphenyl, 2,3-dihydroxyphenyl, 2,3-dimethoxyphenyl and 1-naphthyl;

$R^{11}$ represents H; or an unsubstituted alkyl radical selected from the group consisting of methyl, ethyl, propyl, l-methylethyl, butyl, l-methylpropyl, 2-methylpropyl, 1,1-dimethylethyl, pentyl, 1,1-dimethylpropyl, 1,2-dimethylpropyl, 2,2-dimethylpropyl, hexyl, and 1-methylpentyl; or an unsubstituted cycloalkyl radical selected from the group consisting of cyclopropyl, cyclobutyl, cyclopentyl, cyclohexyl, cycloheptyl, cyclooctyl, cyclopentenyl, cyclohexenyl, cycloheptenyl and cyclooctenyl; or an aryl radical selected from the group consisting of phenyl, 3-hydroxyphenyl, 3-methoxyphenyl, 2,3-dihydroxyphenyl, 2,3-dimethoxyphenyl and 1-naphthyl; or an unsubstituted heteroaryl radical selected from the group consisting of pyrrolyl, furyl, thienyl, pyrazolyl, imidazolyl, pyridinyl, pyridazinyl, pyrimidinyl, pyrazinyl, pyranyl, indolyl, indazolyl, purinyl, pyrimidinyl, indolizinyl, quinolinyl, isoquinolinyl, quinazolinyl, carbazolyl, phenazinyl and phenothiazinyl; or an aryl radical which is bonded via $C_{1-3}$-alkylene and is selected from the group consisting of phenyl, 3-hydroxyphenyl, 3-methoxyphenyl, 2,3-dihydroxyphenyl, 2,3-dimethoxyphenyl and 1-naphthyl; or an unsubstituted heteroaryl radical which is bonded via $C_{1-3}$-alkylene and is selected from the group consisting of pyrrolyl, furyl, thienyl, pyrazolyl, imidazolyl, pyridinyl, pyridazinyl, pyrimidinyl, pyrazinyl, pyranyl, indolyl, indazolyl, purinyl, pyrimidinyl, indolizinyl, quinolinyl, isoquinolinyl, quinazolinyl, carbazolyl, phenazinyl and phenothiazinyl; or an acyl radical $C(O)R^{12}$; or a sulfonyl radical $S(O_2)R^{13}$;

$R^{12}$ represents H; or an unsubstituted alkyl radical selected from the group consisting of methyl, ethyl, propyl, 1-methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, and 1-methylpentyl; or an aryl radical selected from the group consisting of phenyl, 3-hydroxyphenyl, 3-methoxyphenyl, 2,3-dihydroxyphenyl, 2,3-dimethoxyphenyl and 1-naphthyl;

$R^{13}$ represents H; an unsubstituted alkyl radical selected from the group consisting of methyl, ethyl, propyl, 1-methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, and 1-methylpentyl; or an aryl radical selected from the group consisting of phenyl, 3-hydroxyphenyl, 3-methoxyphenyl, 2,3-dihydroxyphenyl, 2,3-dimethoxyphenyl and 1-naphthyl; and $R^{14}$ represents H, F, Br, I, Cl, OH, SH, $NH_2$, $NO_2$, $CH_3$, $C_2H_5$, $OCH_3$, $OC_2H_5$, or $OCF_3$;

or a physiologically acceptable salt thereof formed by protonation of a nitrogen atom thereof with a physiologically acceptable acid, with the proviso that the following compounds:

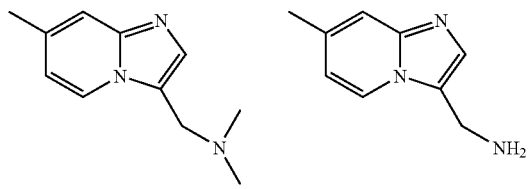

are excluded.

* * * * *